United States Patent [19]

Dahl

[11] Patent Number: 5,308,758
[45] Date of Patent: May 3, 1994

[54] METHOD AND APPARATUS FOR STUDY OF GAS-PHASE AND GAS-BORNE AGENTS

[75] Inventor: Thomas A. Dahl, Boston, Mass.

[73] Assignee: Tufts University, Boston, Mass.

[21] Appl. No.: 959,311

[22] Filed: Oct. 9, 1992

[51] Int. Cl.$^5$ .......................... C12Q 1/24; C12M 1/04
[52] U.S. Cl. ........................................ 435/30; 435/29;
   435/31; 435/34; 435/284; 435/291; 435/299;
   435/313
[58] Field of Search ...................... 435/29–31,
   435/34, 39, 4, 284, 291, 299, 313

[56] References Cited

U.S. PATENT DOCUMENTS

| | | | |
|---|---|---|---|
| 3,127,329 | 3/1964 | Andersen | 435/30 X |
| 3,690,837 | 9/1972 | Witz et al. | 435/30 X |
| 3,713,987 | 1/1973 | Paik et al. | 435/30 |
| 3,741,877 | 6/1973 | Shaufus et al. | 435/30 |
| 4,092,221 | 5/1978 | Schlichting, Jr. | 435/30 |
| 4,734,371 | 3/1988 | Schmolke et al. | 435/284 |
| 4,735,899 | 4/1988 | Stuart et al. | 435/29 |
| 5,155,019 | 10/1992 | Sussman et al. | 435/34 |

OTHER PUBLICATIONS

Schiff et al., 142 *Mutation Research* 41, 1985, "Evidence of DNA Repair in Organ Cultures of Hamster Tracheal Epithelium Following Exposure to Gas Phase Singlet Oxygen".

Dahl et al., 46(3) *Photochemistry and Photobiology* 345, 1987, "Pure Singlet Oxygen Cytotoxicity for Bacteria".
Dahl et al., "Pure Singlet Oxygen Toxicity in Mammalian Cells", *Posters* 10.3, Ed. Blough and Zepp, in "Effects of Solar Ultraviolet Radiation on Biogeochemical Dynamics in Aquatic Environments: Report of a Workshop", Marine Biological Laboratory, Woods Hole, Massachusetts, Oct. 23–26, 1989.
World Precision Instruments, Advertisement entitled "Environmental Chamber: in vitro tissue experiments".

*Primary Examiner*—James C. Housel
*Assistant Examiner*—Krisanne M. Thornton
*Attorney, Agent, or Firm*—Lyon & Lyon

[57] ABSTRACT

Method and apparatus for exposing biological materials to gas-phase or gas-borne agents, including the steps of providing a chamber for supporting said biological materials, said chamber including wicking means configured and arranged to hold said biological materials and provide said cells with a wetting medium while allowing said gas-phase or gas-borne agents to directly interact with said biological materials, humidifying said chamber to a humidity between 95% and 100%, inclusive, placing said biological materials in said chamber on said wicking means, exposing said biological materials in said chamber to one or more said gas-phase or gas-borne agents while maintaining said humidity between 95% and 100%, inclusive, and assessing the effect of said exposing on said biological materials.

14 Claims, 7 Drawing Sheets

METHOD AND APPARATUS FOR STUDY OF GAS-PHASE AND GAS-BORNE AGENTS

BACKGROUND OF THE INVENTION

This invention relates to apparatuses and methods for determining the effect of various gaseous agents on biological materials.

Schiff et al., 142 *Mutation Research* 41, 1985, describe an apparatus for measuring the effect of singlet oxygen on tracheal explants. The apparatus includes a chamber which contains a dish placed on a platform rocker which is rocked approximately 10 times per minute to allow the explants to alternate between immersion in culture medium and contact with the gas-phase.

Dahl et al., 46 *Photochemistry and Photobiology* 345, 1987, describe an apparatus for generation of singlet oxygen which is partially humidified by use of a buffer reservoir.

Dahl et al., Pure Singlet Oxygen Toxicity in Mammalian Cells, *Poster* 10.3, Ed. Blough and Zepp, "Effects of Solar Ultraviolet Radiation on Biogeochemical Dynamics in Aquatic Environments: Report of a Workshop Marine Biological Laboratory", Woods Hole, Mass., Oct. 23–26, 1989, describe modifications to the apparatus of Dahl et al., 1987, which include carrying out exposures in a humidified chamber, and keeping the membrane filters wicked from beneath with growth medium-saturated filter paper.

World Precision Instruments, advertisement entitled "Environmental Chamber", describes an apparatus useful for in vitro tissue experiments in which the gas content of the liquid medium in a chamber can be regulated.

SUMMARY OF THE INVENTION

This invention features an improved apparatus for allowing gaseous exposure of sensitive biological materials to gas-borne or gas-phase agents. Applicant has found that prior apparatuses and methods were not suitable for use with such biological materials since the biological materials would become desiccated and die. To this end, Applicant has designed an apparatus which maintains the humidity of a chamber containing those biological materials at or near 100%, such that the biological materials remain viable in an otherwise normal gaseous environment. In addition, nutrients are provided to the biological materials in a manner which does not prevent direct gaseous contact with the biological materials. This allows a true assessment of the effect of one or more gas-borne or gas-phase agents in the gas in contact with these biological materials.

Thus, in a first aspect, the invention features a method for exposing biological materials to gas-phase or gas-borne agents. The method includes providing a chamber for supporting the biological materials. This chamber may include a wicking means configured and arranged to hold the biological materials and provide them with a wetting medium, while allowing the gas-phase or gas-borne agents to directly interact with the biological materials. The method further involves humidifying the chamber to a humidity between 95% and 100%, inclusive, placing the biological materials in the chamber on the wicking means, and exposing the biological materials in the chamber to one or more gas-phase or gas-borne agents while maintaining the humidity between 95% and 100%, inclusive. After this exposure, the method involves assessing the effect of such exposure on the biological materials.

Biological materials include cells and subcellular, cell-derived, and cell model systems (e.g. microsomal, synaptosomal, and liposomal preparations).

In a related aspect, the invention features an apparatus for use in the above method.

In preferred embodiments, the method involves humidifying with a humidifying means which includes a first gas-washing means, including water through which a gas is passed in a manner which saturates the gas with water, and a second gas-washing means (also including water) through which gas from the first gas-washing means is passed in a manner to condense excess water in that gas and to provide gas with a humidity between 95% and 100%, inclusive; the first gas-washing means includes water heated to between 40°–60° C., and the second gas-washing means includes water at the ambient temperature of the sample chamber (e.g. between about 20°–25° C.); the biological materials are held in a monolayer on the wicking means; and the biological materials are selected from the group consisting of tissue culture cells, microbial cells, a population of isolated naturally occurring cells, and cells in a tissue section.

In other preferred embodiments, the wicking means includes a soft agar layer, or a membrane filter; the assessing step includes staining the biological materials or measuring the activity of an enzyme associated with those biological materials; and the exposure is for a period of time which does not cause dessication of the biological materials e.g., less than 24 hours, 12 hours, and most preferably less than two hours.

By "gas-phase" or "gas-borne" agent is meant to include any gas (or any gas which may include non-gaseous components) which may be toxic to certain biological materials.

Those in the art will recognize that the humidity of the chamber can be measured by standard procedure. Generally, however, such humidity will be at or close to 100% if the gas provided to the biological material is passed through the two gas-washing means described above.

Other features and advantages of the invention will be apparent from the following description of the preferred embodiments thereof, and from the claims.

DESCRIPTION OF THE PREFERRED EMBODIMENTS

The drawings will first briefly be described.

BRIEF DESCRIPTION OF THE DRAWINGS

FIG. 1A is an isometric view of a humidification chamber with a sample stage and a wicked sample filter, both of which are shown in more detail in FIG. 1B; and FIG. 1C is an isometric view of a complete apparatus containing the humidification chamber;

FIG. 2D is an isometric view of the housing and various controls for a humidification apparatus, and FIG. 2E is an isometric view partially in cross-section of a disposable insert for a humidification apparatus;

HUMIDIFICATION CHAMBER

Figure 1A:
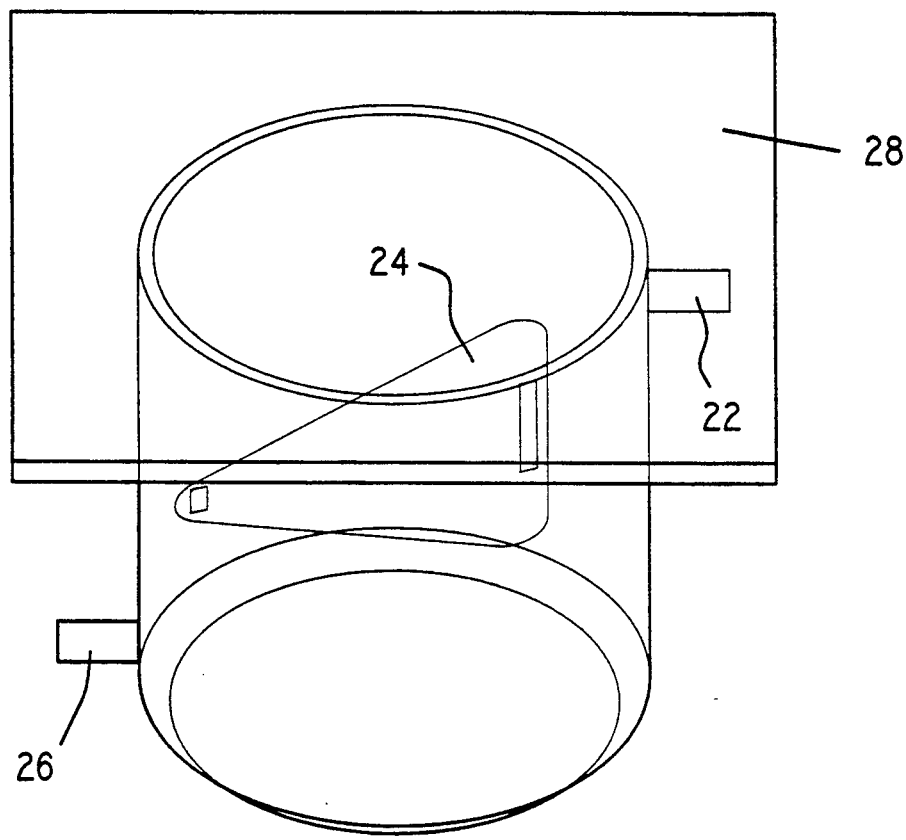
FIGS. 1A–1C are diagrammatic representations of a humidifying apparatus of the invention, specifically.
Figure 1B:
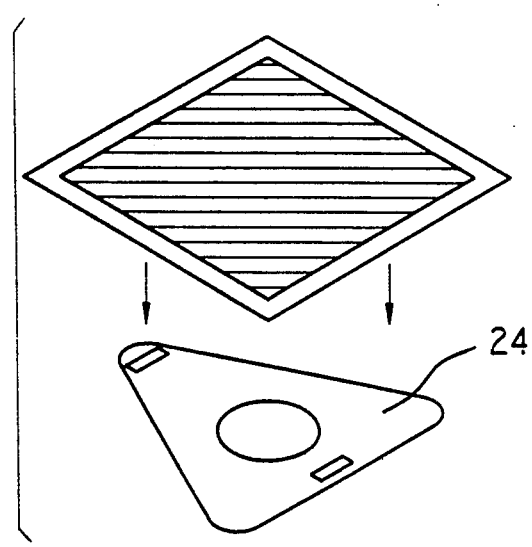
Figure 1C:
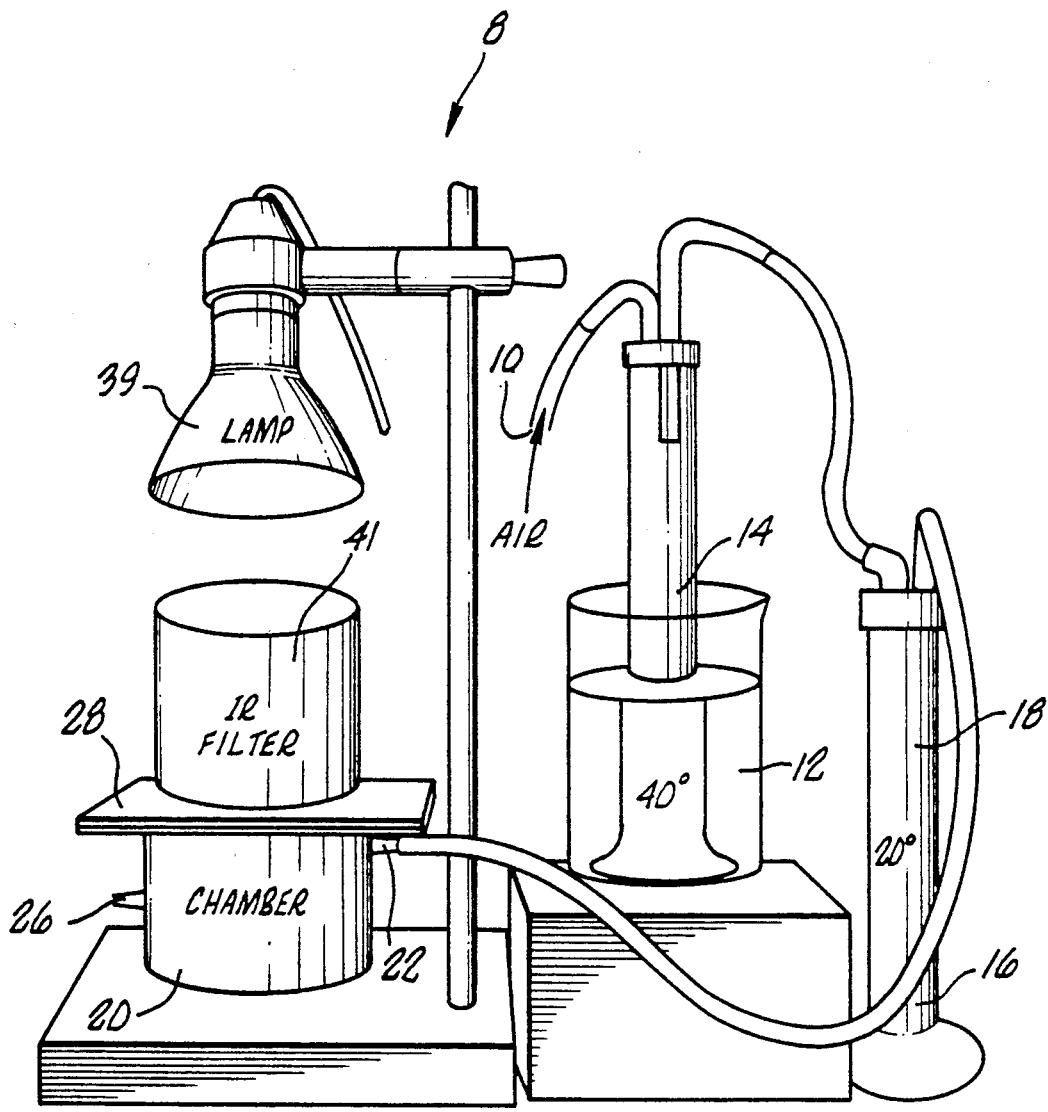

A prototype for an apparatus to examine the exposure of biological materials to gas-phase or gas-borne agents, for in vitro, in vivo, and in situ toxicology studies, screening of suspected toxicants, or screening agents of unknown biological/toxicological response is now described. The apparatus is sufficiently versatile to include living microbial samples, isolated tissues, and cultured primary cells or cell lines as targets for investigation.

The primary difficulty in exposing biological samples to gas-phase agents is desiccation of the material. This is especially true with removal of the bulk medium from cellular or tissue samples to allow gaseous agents to impinge directly on target surfaces. The key features of an exposure apparatus include a design to prevent sample desiccation during exposure to gaseous agents in the absence of extracellular medium. Results observed in such a system can be attributed solely and unambiguously to events initiated by the agent or mixture of agents under investigation. Further, all exposed parts of the sample receive the same magnitude of exposure per surface area per time interval, which supports kinetic studies critical to establishing dose responses, risk assessment, and safety guidelines. Versatility in this system derives from two sources: 1) the chamber will accept virtually any biological sample for in vitro, in vivo, and in situ investigations; and 2) gaseous agents or mixtures of agents are introduced to the samples by simply adding them to the airstream flowing through the chamber. The various combinations enabled by these features provides an essentially unlimited array of investigatorial possibilities for environmental studies, including air pollutants and gas components in aqueous environments, risk assessment for known or suspected toxic agents, establishing health and safety guidelines for worker/consumer exposure, screening and discovery of pharmaceuticals, including inhalation anesthetics and upper respiratory-active agents and replacement of whole animal studies with in vitro says in the cosmetics and drug testing industries for assessing toxic and allergic responses.

Adequate moisture in the sample environment is maintained by humidifying the air inside the exposure chamber to saturation (i.e. 100% humidity) and, in work with cultured cells, by providing a moist surface, such as a thin soft agar layer, for the samples to rest on. Humidification affords a rapid water-transfer equilibrium between the sample and the gas-phase, so there is no net loss of water from the sample surface. In addition, the soft agar layer or other moist surface material effectively "wicks" the sample from below, providing both water and a potential source of nutrients to the sample during exposure, without intervening between or interfering with the sample-gas interface at the surface above.

EXAMPLE 1

Water Bubbler Humidified Chamber

Referring to FIGS. 1A-1C, 4 and 5, humidification chamber 8 consists of a 1 L polycarbonate jar 20 fitted with two teflon nozzles 22, 26, and a glass sample stage 24 supported by bamboo pegs (not shown) inserted into the sides of the jar in a horizontal planar arrangement. The inflow nozzle 22 is fitted to an gasstream of water-saturated air. Compressed air is bubbled through water 12 heated to 40°-60° C. in a gas-washing bottle 14 at about 5-10 ml/s. Effluent from this bottle is bubbled through water 16 at room temperature (20°-25° C.) in a second gas-washing bottle 18 to condense excess moisture. Effluent from the second bottle reaches chamber 20 through inflow nozzle 22, circulates downward past glass stage 24 (FIGS. 1A, 1B and 5) which has a generally triangular shape to allow the passage of air, and out through outflow nozzle 26. The machined edge of the jar opening is covered with a 3 mm thick rolled-glass plate 28 to seal the chamber during illuminations and attenuate UV penetration to the samples. Optical filters (IR=15 cm water column; cut-off=4 mm Schott OG-525) in the light path are placed atop this glass plate. Optical filters and illumination are a part of the apparatus for singlet oxygen ($^1O_2$) generation, specifically, but are not required for humidification of the chamber.

EXAMPLE 2

Other Chambers

Figure 2A:
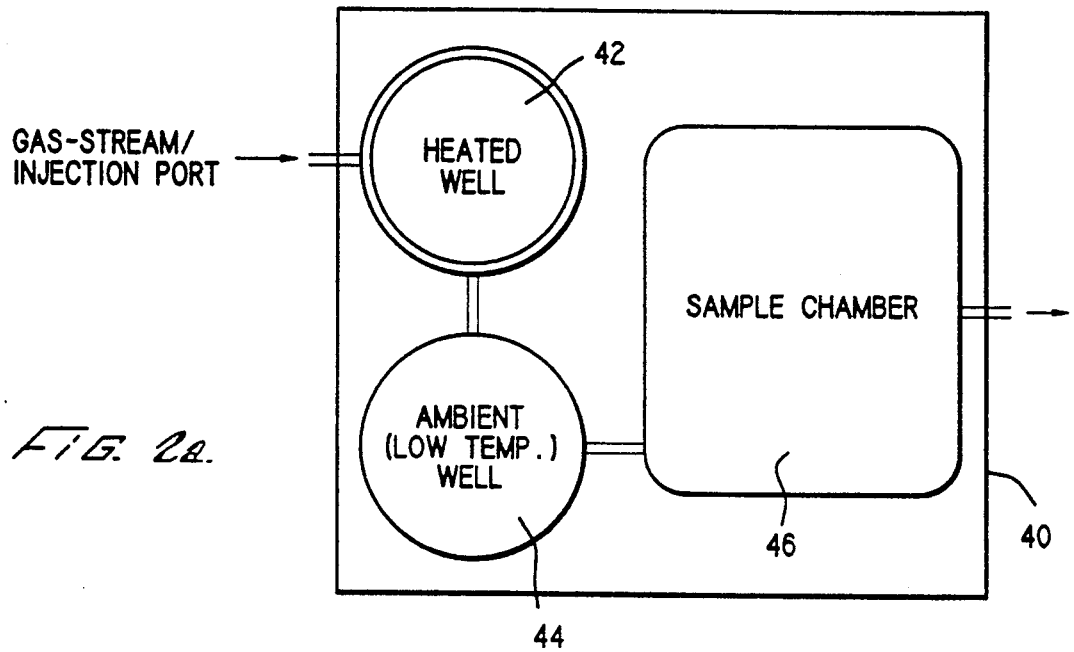
FIGS. 2A–2E are schematic representations of various embodiments of the present invention, specifically, FIG. 2A discloses apparatus with a single sample chamber, FIG. 2B discloses apparatus with two sample chambers, and FIG. 2C discloses apparatus with a sample and a control chamber.
Figure 2B:
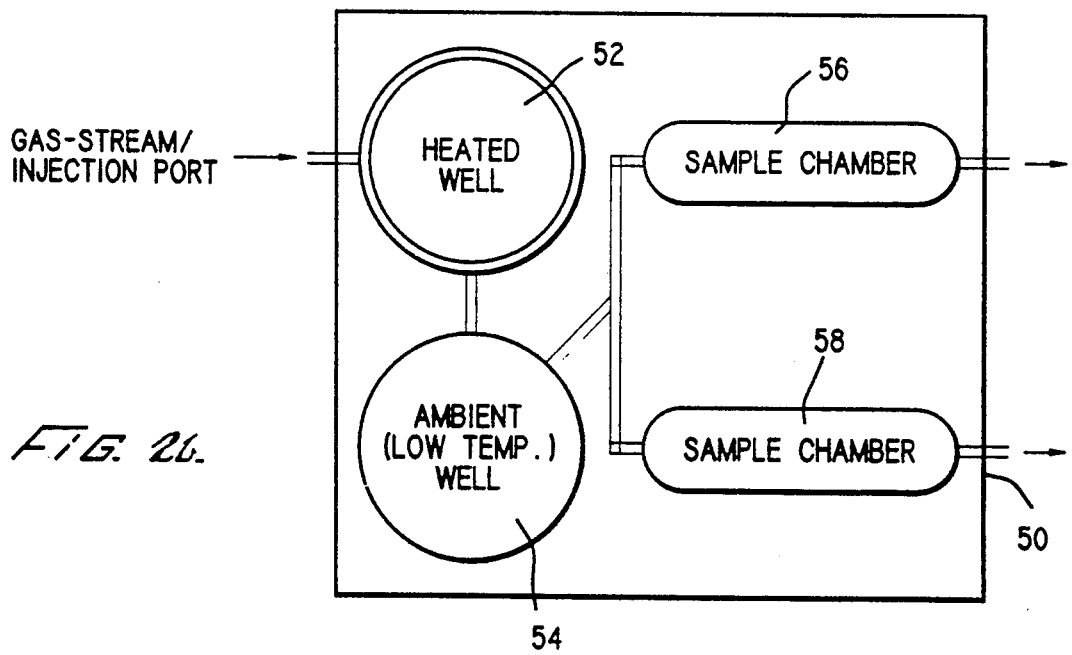
Figure 2C:
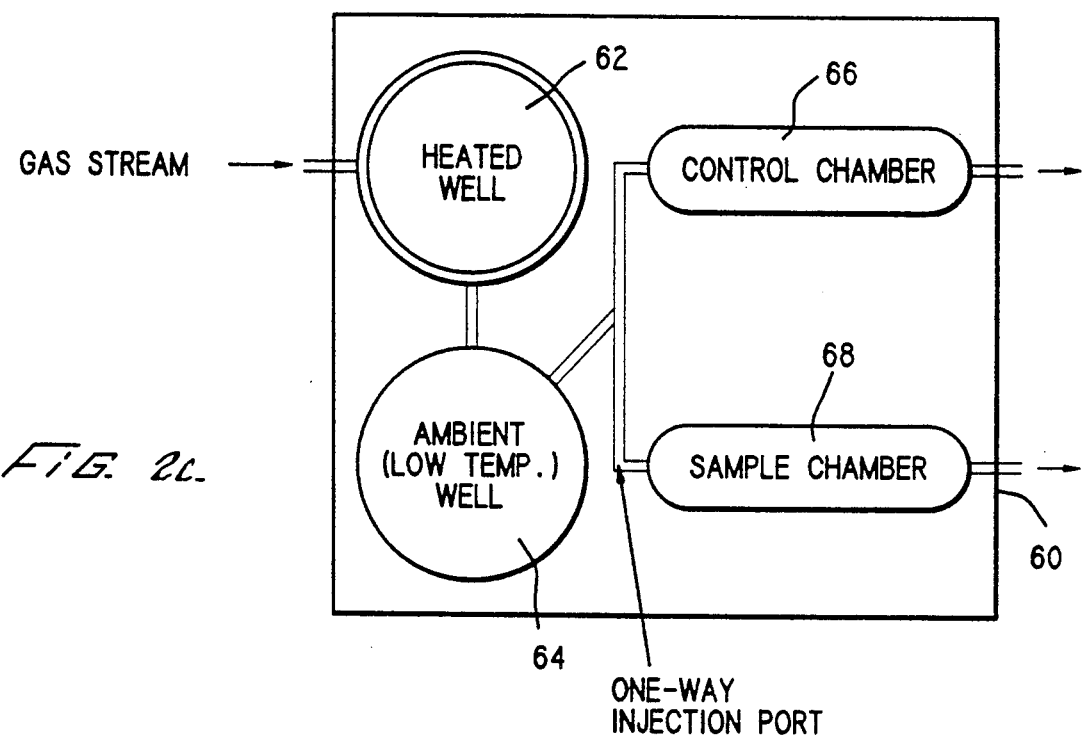

Referring to FIGS. 2A-2E, alternative apparatuses of the present invention are shown. Specifically, referring to FIG. 2A there is shown a humidification apparatus 40 having a heated well 42 and an ambient or low temperature well 44 connected in series to a sample chamber 46. Similarly, in FIG. 2B there is shown a humidification apparatus 50 having a heated well 52 and an ambient or low temperature well 54 which leads to two parallel sample chambers 56 and 58 to allow simultaneous analysis of two samples. Referring to FIG. 2C there is shown a humidification apparatus 60 having a heated well 62, an ambient or low temperature well 64 and two chambers, one of which is used as a control chamber 66, and another as a sample chamber 68, allowing simultaneous assay of known cells with a sample cell or of a gaseous agent with its carrier gasstream.

Figure 2D:
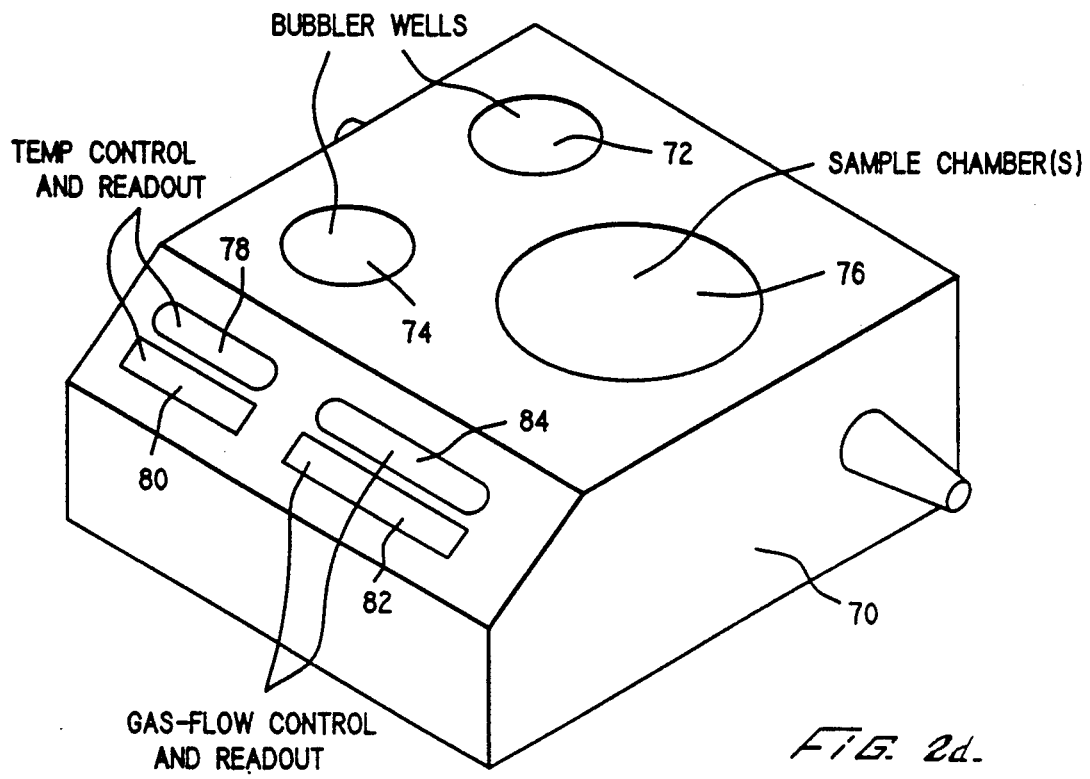

Referring to FIG. 2D there is shown in diagrammatic form a humidification apparatus 70 having two bubbler wells 72 and 74, for humidifying a gas stream, and a sample chamber 76, all of which can be accessed from the upper portion of apparatus 70 to allow alteration of the content of the bubbler wells, or the sample chamber. In addition, also provided is temperature control 78 and temperature readout 80, so that the appropriate temperature in each of the bubbler wells can be determined and controlled. There is also provided a control 82 for regulating gas flow, which is indicated by an indicator 84.

Figure 2E:
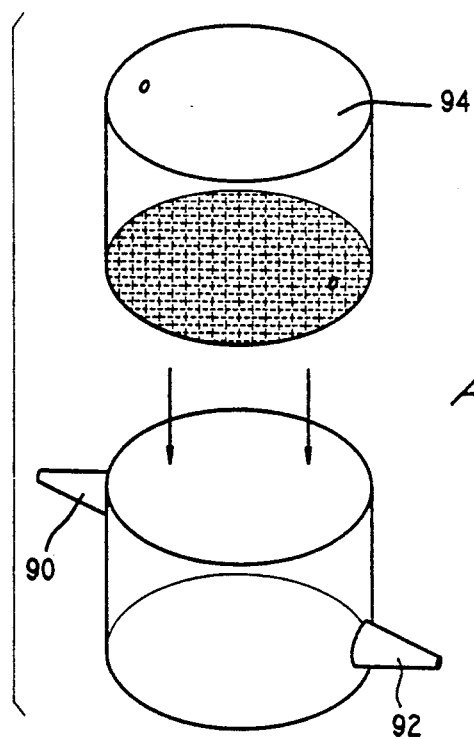

Referring to FIG. 2E there is shown a disposable insert type chamber for use in apparatus 70 which has an inlet 90 and an outlet 92, and a cell culture insert 94 which can be removed after each sample assay. Such inserts are especially useful when samples are assayed in the presence of persistent toxicants which are difficult to remove from the sample chamber after an experiment is performed.

It will be apparent to those skilled in the art that gas flow can be regulated by any standard pump using a regulator valve. In addition, each component, such as the bubbler wells, and sample containers may be modularly attached to a humidification apparatus of the present invention. Sophisticated temperature controllers and sealed chambers can be provided in the apparatus, and the two bubbler chambers thermostatically controlled and sealed from one another to allow appropriate temperature control. It is preferred that insulated Teflon tubing be used throughout the apparatus to ensure no gas contamination.

Methods

An important component of gas-phase exposure is removal of bulk medium from the samples to permit direct interaction between the gas-phase and the target surface. Tissue sections are easily blotted to accomplish this goal immediately prior to transfer into the exposure chamber. Cultured cells and microbial samples generally require deposition or attachment to a carrier surface, such as membrane filters, prior to placement of the carrier onto sample stage 24. This additional step greatly enhances ease of handling and sample recovery following exposure. The use of membrane filters specifically, in contrast to other potential carriers such as glass cover slips, improves the ease of external medium removal from the exposed sample surface, and equally as important, allows wetting (from beneath) of the cells via the moistened "wick" interposed between the sample and the glass stage. This last consideration seems to be most important for samples comprised of monocellular (or less) cell layers, which provide the further advantage of completely uniform and consistent exposure for all parts of the target.

EXAMPLE 3

Eucaryotic Cell Preparation

Hepatocytes were isolated from male B6C3F1 mice (30-35 g) by two stage collagenase perfusion of the liver via the portal vein as previously described (Klaunig et al., 17 *In Vitro* 913, 1981). Isolated cells (>95% hepatocytes which were 90-95% viable as determined by trypan blue exclusion) were plated onto collagen-coated polycarbonate membrane filters at a density of $5 \times 10^4$ cells/cm$^2$ in hepatocytes culture medium (Leibovitz' L-15 medium supplemented with 10% fetal bovine serum, 50 µg/ml gentamicin sulfate, and 1 µM dexamethasone). Greater than 95% of the cells attached to collagen-coated filters excluded trypan blue dye, and greater than 98% stained positive for glucose-6-phosphatase, a marker for adult hepatocytes (Eckl et al., 132 *J. Cell Physiol.* 363, 1987).

In another example, squamous carcinoma cell line, FaDu (ATCC HTB43) and the rat basophilic leukemia cell line, RBL (ATCC CRL1378) were grown in RPMI medium supplemented with 10% fetal bovine serum. Chinese hamster lung fibroblasts, V79, were obtained from Prof. Nancy Oleinick (Case Western Reserve University, Cleveland) and cultured in McCoy's 5A medium supplemented with 10% calf serum.

Cells were either seeded on collagen-coated polycarbonate membrane filters and incubated overnight to allow attachment, or deposited with gentle vacuum filtration on uncoated filters and washed off filters immediately following treatment. Sterile rat tail collagen was prepared as previously described (Meyer et al., 49 *Cancer Research* 5907, 1989). Polycarbonate membrane filters (25 mm diameter, Nucleopore Corp.) were dipped in the collagen, air-dried, and washed with culture medium prior to use.

As an alternative plating method, cells were seeded on membrane filters fixed in culture plate "inserts", which are plastic holders designed to fit within the wells of a 6-well microtiter plate (25 mm diameter, Anotec Separations, New York). 0.5 ml collagen solution was spread on the external polycarbonate membrane surface and air-dried inverted under UV light. Primary hepatocytes were allowed to attach to the coated filters for 4 hours, then refed with fresh culture medium (2 ml/35 mm well) and cultured in a humidified, 100% air incubator at 36.5° C. overnight before use. FaDu and V79 cells were allowed to attach overnight in a 1:1 mixture of fresh and conditioned growth media in a humidified 5% $CO_2$ incubator at 37° C. before use. RBL cells were handled as FaDu and V79, except that no collagen was necessary for RBL attachment to polycarbonate.

When inserts were used, cells were seeded on the external filter surface by inverting the inserts in the wells of a six-well culture plate. Cells attached to filters or inserts were examined by phase-contrast microscopy, and observed to be attached in a monolayer or less, depending on number of attached cells.

For cells deposited on filters without attachment, filters were not coated. Cells were rinsed, suspended and diluted in phosphate-buffered saline (PBS), and the suspension spread on membrane filters (25 or 47 mm diameter) in a glass filtration apparatus, before applying a gentle vacuum. In most cases a piece of sterile filter paper was interposed between the membrane filter and the fritted glass filtration stage to cushion the transition from ambient to lower pressures. Examination by phase-contrast microscopy showed individual spheroid cells. Measurements of trypan blue-stained vacuum-filtered cells generally showed <5% staining following filtration.

Measurements of trypan blue-stained vacuum-filtered cells generally showed <5% staining following filtration (i.e., the cells retained their liability). Cell integrity before and after gaseous exposure was measured by standard assays. For example, for membrane leakage assays (lactate dehydrogenase=LDH, or trypan blue exclusion) $10^5$–$10^6$ cells were exposed per 25 mm diameter filter, giving essentially confluent filter coverage to a monolayer*1/. For colony formation, $10^2$–$10^3$ cells were exposed per filter. For transfer to the exposure chamber, filters with attached cells were rinsed twice in sterile PBS, and the remaining droplets of saline removed by blotting the filter edge lightly on clean, sterile filter paper. For filters with unattached cells, the filters were transferred from the filtration unit directly to the exposure chamber. Seeded filters were placed cell-side up on top of either a thin layer of soft agar (0.5%) or a piece of culture medium-soaked Whatman #1 filter paper on the glass stage of the exposure chamber. Inserts were rinsed similarly and remaining saline removed by mild vacuum of the clinging droplet through a clean, sterile glass pasteur pipet. Inserts were placed in the chamber cell-side down, without filter paper, since 1 mm "feet" were provided on the insert to prevent contact with the stage. One-half to 1 ml of PBS was pipetted into the insert to maintain moisture, analogous to the "wicks" described above.

\* The exact number of cells per filter depends on the cell type and size, e.g., approximately 6–7×10⁵ murine primary hepatocytes form a confluent monolayer on a 25 mm filter. FaDu cells, at about half the hepatocyte cell diameter, cover this area with a little over 3×10⁶ cells.

Cells attached overnight or deposited on membrane filters without allowing attachment were measured under both low (100×) and high (200×) magnification with an objective micrometer scaled in 10 μm divisions. Cells appeared spheroid, rectangular, trapezoidal or irregular in shape. For RBL cells, which often have minute projections from a main cell body, only the area of the cell body was considered. The surface area for gas-phase exposure was determined as the projected area (i.e., the area of a two-dimensional representation of the cell viewed from above). For cells that were irregular in shape, measurements were made subdividing the cell into more regular subunits and the subunits summed. For cells that were measured independently as attached and unattached cells, the measurements by each method were in excellent agreement.

EXAMPLE 4

Microbial Cell Preparation

Microbial cells such as bacteria were harvested by centrifugation of growth culture suspensions, cell pellets washed by resuspension in physiological saline (PSS) or PBS, repelleted, resuspended and serially diluted in PSS or PBS. Cell suspensions were vigorously vortexed at each washing and dilution step to ensure disruption of chains, clusters, or other cell aggregates, resulting in suspensions of individual cells. The suspensions were inspected microscopically to verify this before filtering aliquots with membrane filters to collect cells and remove bulk liquid (Dahl et al., 46 Photochemistry and Photobiology 345, 1987).

EXAMPLE 5

Gas Exposure

As one example of a gas to be tested, singlet oxygen was chosen. Those in the art will recognize that other gas-phase or gas-borne agents may be generated and used in an analogous manner.

Generation of $^1O_2$ for mammalian cell exposure follows the same principles and practices previously described for other cellular targets (Dahl et al., 46 *Photochem Photobiol* 345, 1987), i.e., physical separation of dry photosensitizer from cells deposited in a monolayer or less during illumination. For exposure of cells on membrane filters, glass spacers of defined thickness were placed at two ends of the chamber stage and the photosensitizer plate rested on these spacers. For exposure of cells on inserts, the photosensitizer plate was placed dye-side up on the chamber stage, and the insert placed cell-side down over the photosensitizer. Illuminations used a tungsten-filament lamp 39 (FIG. 1C), as previously described (Dahl et al., 46 *Photochem Photobiol* 345, 1987) with filters 41 (FIG. 1C) or inserts spaced symmetrically within the incident light. Increases in the $^1O_2$ flux were accomplished by decreasing the distance between illumination source 41 and humidification chamber 20.

Endpoints for determination of cell survival included assays for membrane destabilization (LDH leakage out of damaged cells or trypan blue leakage in), vital dye (neutral red) staining of cells with intact active transport systems, and colony formation by individual cells. For leakage assays, samples were incubated 2 hours following treatment, prior to measurements. For neutral red (NR) staining, cells were incubated with growth medium, containing NR, 24 hours following $^1O_2$ treatment, prior to scoring. For subsequent feeding of cells attached to inserts, the inserts were reinverted into 2 ml growth medium in the bottom of each well. Membrane filters with unattached cells were placed cell-side down into fresh growth medium and agitated gently in wells of 6-well microtiter plates. Polycarbonate filters floated on the medium while cells settled onto the well bottom, where they subsequently attached. Filters were removed from wells to allow gas exchange between incubator and medium. Colonies were counted after incubation of samples for 4–6 cell generation times (3–7 d, depending on cell type).

The calibration of cell exposure was based on a zero-order reaction model, in which the rate of target reaction was determined solely by the flux of $^1O_2$ reaching a distance corresponding to the target surface (Dahl et al., 46 *Photochem Photobiol* 345, 1987). Because $^1O_2$ generation by dry photosensitizer is continuous during illumination, this flux is constant for the duration of illumination. Cell exposures in this study were calibrated with the reaction of 2,5-dimethyl furan (DMF) with $^1O_2$ in acetonitrile, starting with a DMF concentration of 0.1M, which is 20 times the β-value (Dahl et al., 46 *Photochem Photobiol* 345, 1987). For the comparison of results between confluent cells and sparsely plated cells (where most of the sample is empty space), flux measurements were converted from collisions per sample to collisions per cell, by consideration of the relative exposed surface areas of the DMF solution and cellular targets.

The following results were obtained. Maintenance of adequate moisture in the exposed cells' environment and attenuation of IR exposure eliminated desiccation of samples. Either in the absence of illumination or under illumination without exogenous photosensitizer, most cells supported on membrane filters maintained complete viability for up to 2 hours in the exposure apparatus (See FIG. 3; some data not shown). FaDu survival was determined by colony formation, and is representative of the other cell lines used. Survival for the murine primary hepatocytes was measured by loss of membrane integrity, monitoring the leakage of LDH activity into extracellular medium. The hepatocytes demonstrated toxicity through an endogenous photosensitizer when illuminated with white light from a tungsten lamp in the absence of exogenous $^1O_2$. This endogenous photosensitization was eliminated prior to $^1O_2$ exposures by the inclusion of an OG-525 optical cut-off filter in the light path. The output spectra of the illumination source measured with an Optronics Model 742 Spectroradiometer with and without the cut-off filter provide an-approximate wavelength range, from 350 nm to 500 nm, in which absorption by an endogenous cellular photosensitizer is critical. None of the established cell lines displayed any endogenous photosensitization.

Figure 3:
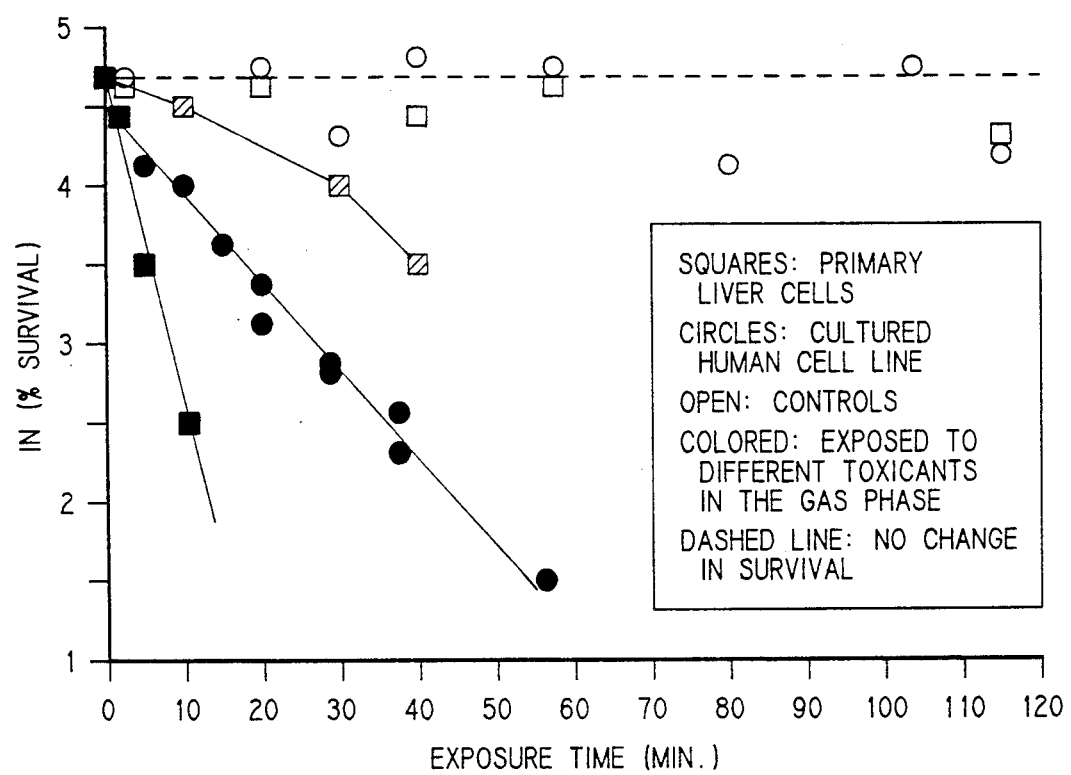
FIG. 3 is a graphical representation showing the effect of singlet oxygen on a cultured human squamous cell carcinoma cell lines (FaDu) and murine primary hepatocytes, specifically, the squares represent primary liver cells and circles represent cultured human cell lines, open circles or squares are controls, filled circles or squares illustrate various exposures to different toxicants in the gas-phase, and the dashed line represents no change in survival.
Figure 4:
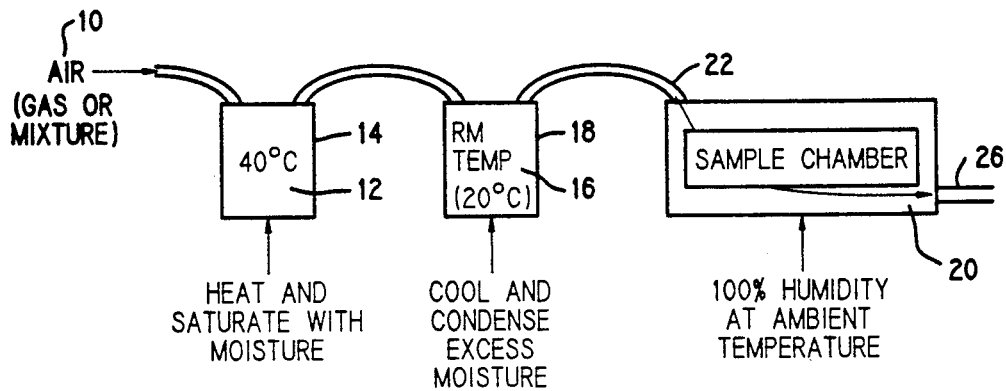
FIG. 4 is a diagrammatic representation of a humidification apparatus.
Figure 5:
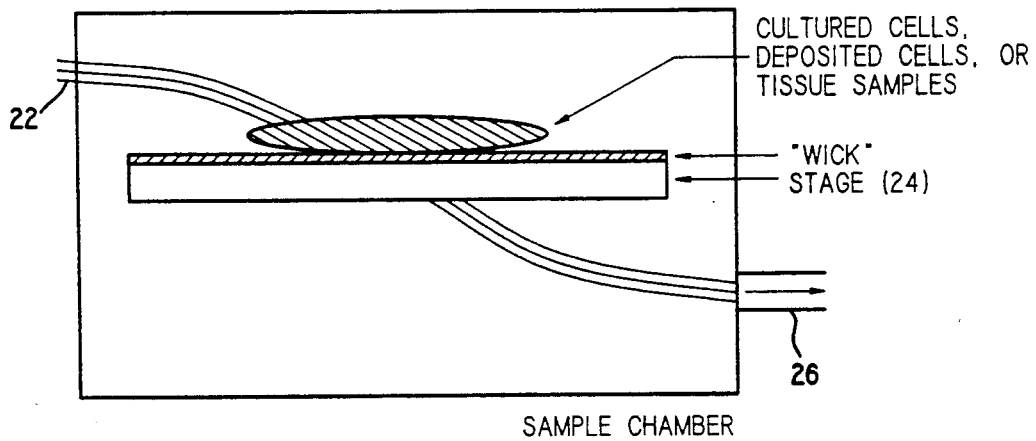
FIG. 5 is a diagrammatic representation of the flow of gas through a humidification apparatus.

The lethal cytotoxicity of $^1O_2$ to FaDu and primary hepatocytes is shown in FIG. 3. Results with other cell types, regardless of the survival endpoint measured, demonstrated simple first-order decline in survival with increased duration of steady-state $^1O_2$ exposure. FIG. 3 is plotted as ln (survival) versus time, so the slopes of these curves provide an apparent first-order rate constant for cell killing by $^1O_2$ Along with the $^1O_2$ flux measurements and estimates of the average projected cell surface area exposed to $^1O_2$ this information can be used to calculate the amount of $^1O_2$ required to kill a cell, according to the relationship $$N_L = \frac{F_\Delta S_c}{k_L}$$

where NL is the amount $^1O_2$ required to kill a cell, $F\Delta$ represents the $^1O_2$ flux reaching the cell surface, Sc is the exposed surface area of the cell, and kL is the first-order rate constant for cell inactivation.

For experiments with primary murine hepatocytes, $F\Delta$ was maintained at 0.39 μmol/cm² minutes. These cells have an average cell diameter of 20 μm, giving a projected surface area $S_c$ of 314 μm²/cell. From the data in FIG. 3, $k_L=0.223$ min$^{-1}$, yielding $5.4 \times 10^{-6}$ μmoles $^1O_2$ per cell killed or $3.3 \times 10^{12}$ molecules $^1O_2$ colliding per cell killed. A similar calculation for the smaller FaDu cells (Sc=79 μm²/cell), exposed at a higher $^1O_2$ flux (0.98 μmol/cm² min) with $k_L=0.06$ min$^{-1}$ (FIG. 3, Table 1), estimates $8 \times 10^{12}$ molecules $^1O_2$/cell killed. The same result was obtained with a lower $F\Delta$ (0.26 μmol/cm² min) yielding $k_L=0.015$ min$^{-1}$ (Table 1).

on filters in a monolayer or less ensures that all cells receive identical exposure; there is no gradient of gas concentration owing to decay while diffusing through an extracellular medium. In aqueous media, such gas penetration into the suspension medium is highly restricted, relative to its depth, so that the bulk of the sample remains unexposed. This can create a reaction zone which would be only a minute fraction of the total sample even in a cell suspension of only 1 mm depth, the shallowest cell suspensions adapted to gas-phase $^1O_2$ generation (Decuyper-Debergh et al., 225 *Mutation Research* 11, 1989; Wang et al., 52 *Photochem. Photobiol.* 753, 1990). The average net displacement (x) of gas from the surface of a solution or cell suspension depends on quenching (kq) and diffusion (D) constants according to the expression $x=(kq/2D)^{-\frac{1}{2}}$ (adapted from Midden and Wang, 105 *J. Amer. Chem. Soc.* 4129, 1983). For a situation in which all the $^1O_2$ quenching in the system is assumed to be due to $H_2O$ ($kq=2.5 \times 10^5$ s$^{-1}$, Lindig and Rodgers, 1979; $D=2\times 10^{-5}$ cm² s$^{-1}$, CRC *Handbook of Chemistry and Physics*, 71$^{st}$ Edition, p. 6-151) the mean pathlength $\gtrsim 100$ nm. Taking the mean gas pathlength to represent the mean reaction zone, the relative exposure can be approximated by the penetration of gas into a sample of total depth .1 mm: $10^{-7}$

TABLE 1

| | Flux, rate, and cell size parameters for calculation of lethal singlet oxygen exposure. | | | | |
|---|---|---|---|---|---|
| CELL TYPE | ASSAY | APPARENT FIRST-ORDER RATE CONSTANT (min$^{-1}$) | SINGLET OXYGEN FLUX (μmol/cm² min) | CELL SURFACE AREA EXPOSED (μ²/cell) | $^1\Delta_gO_2$ MOLECULES per CELL KILLED |
| Primary Hepatocytes | LDH | 0.223 | 0.39 | 314 | $3.3 \times 10^{12}$ |
| FaDu | Colony Formation | 0.015 | 0.26 | 79 | $8.1 \times 10^{12}$ |
| | NR | 0.055 | 0.98 | 79 | $8.4 \times 10^{12}$ |
| | Colony Formation | 0.059 | 0.98 | 79 | $7.9 \times 10^{12}$ |
| RBL | Colony Formation | 0.112 | 0.98 | 113 | $5.9 \times 10^{12}$ |
| V79 | Trypan Blue | 0.073 | 0.98 | 177 | $1.4 \times 10^{13}$ |
| | Colony Formation | 0.070 | 0.98 | 177 | $1.5 \times 10^{13}$ |

LDH = measurement of lactate dehydrogenase activity in extracellular medium after 2 h post-exposure incubation at 36.5° C.
NR = staining of attached cells with the vital dye, neutral red.
Colony Formation = at least 2 cell divisions during incubation following exposure.
Trypan Blue = staining of non-surviving cells washed off membrane filters after exposure (2 h post-exposure incubation).

Despite differences in cell type exposed and survival endpoint measured, these estimates of the number of $^1O_2$ collisions necessary to inactivate a cell differ by only about a factor of 2. This similarity in values is also demonstrated for other samples in Table 1, all falling within the range $10^{12}-10^{13}$, with the variation between the most sensitive (hepatocytes) and the least sensitive (V79) being approximately a factor of 4. It is also notable that alternate survival endpoints with a single cell type (e.g., FaDu or V79, Table 1) yielded virtually identical estimates of the number of $^1O_2$ collisions necessary to kill the cells.

It is apparent from these data that the apparatus and methods described above allow a gas, such as $^1O_2$ to specifically interact directly with cell surfaces. With $^1O_2$ impinging directly on cells there is no possibility for $^1O_2$ conversion or reaction to secondary cytotoxic species in extracellular media prior to interaction with the cells. This may not be a problem initially with simple buffers as suspension media, although it would certainly be a consideration with more complex media, particularly those containing serum. This is also an heuristic consideration with other gaseous agents whose lifetimes, diffusivities, or reactivities may be affected by extracellular medium.

Direct gas exposure of samples offers additional advantages for quantitation of results. Deposition of cells m/$10^{-3}$ m = $10^{-4}$. This means that 99.99% of cells in a shallow suspension are not exposed to gas $^{+2/}$.

Stirring the sample, assuming all cells are thereby equally exposed, converts this estimate to the fraction of total exposure each cell receives.

Quantitative results require a system in which all cells in the sample can be exposed to the toxic agent, all at the same level of exposure, and the level quantified. These conditions are met by the exposure of cells deposited in a single-depth planar array to direct contact with the toxicant in the apparatus discussed above.

Other embodiments are within the following claims.

I claim:

1. Method for exposing biological materials to gas-phase or gas-borne agents, comprising the steps of:
   providing a chamber for supporting said biological materials, said chamber further comprising wicking means configured and arranged to hold said biological materials and provide said biological materials with a wetting medium while allowing said gas-phase or gas-borne agents to directly interact with said biological materials,
   providing humidifying means for humidifying said chamber,
   humidifying said chamber to a humidity between 95% and 100%, inclusive, placing said biological materials in said chamber on said wicking means, exposing said biological materials in said chamber to one or more said gas-phase or gas-borne agents while maintaining said humidity between 95% and 100%, inclusive, and assessing the effect of said exposing on said biological materials.

2. The method of claim 1, wherein said exposing is for a period less than 2 hours.

3. The method of claim 1, wherein said humidifying means comprises a first gas-washing means comprising water through which a gas is passed in a first gas transporting means in a manner which saturates said gas with water, and a second gas-washing means comprising water through which gas from said first gas-washing means is passed in a second gas transporting means in a manner to condense excess water in said gas to provide gas with a humidity between 95% and 100%, inclusive.

4. The method of claim 3, wherein the water in said first gas-washing means is heated to between 40° C. and 60° C., and the water in said second gas-washing means is at ambient temperature or the same temperature as the sample chamber.

5. The method of claim 1, wherein said biological materials are held in a monolayer on said wicking means.

6. The method of claim 1, wherein said biological materials are selected from the group consisting of a population of isolated naturally occurring cells, and cells in a tissue section.

7. The method of claim 1, wherein said assessing comprises staining said biological materials.

8. The method of claim 1, wherein said assessing comprises measuring the activity of an enzyme associated with said biological materials.

9. The method of claim 1, wherein medium is removed from around said biological materials prior to said exposing step.

10. Apparatus for exposing biological materials to gas-phase or gas-borne agents, comprising:

a chamber for supporting biological materials, and humidifying means for maintaining the humidity of said chamber between 95% and 100%, inclusive;

said chamber further comprising wicking means configured and arranged to hold said biological materials and provide said biological materials with a wetting medium while allowing gas-phase or gas-borne agents to directly interact with said biological materials.

11. The apparatus of claim 10, wherein said humidifying means comprises a first gas-washing means comprising water through which a gas is passed in a first gas transporting means in a manner which saturates said gas with water, and a second gas-washing means comprising water through which gas from said first gas-washing means is passed in a second gas transporting means in a manner to condense excess water in said gas to provide gas with a humidity between 95% and 100%, inclusive.

12. The apparatus of claim 11, wherein the water in said first gas-washing means is heated to between 40° and 60° C., and the water in said second gas-washing means is at ambient temperature or the same temperature as the sample chamber.

13. The apparatus of claim 10, wherein said chamber further comprises said biological materials, wherein said biological materials are held in a monolayer on said wicking means.

14. The apparatus of claim 10, wherein said chamber further comprises said biological materials, wherein said biological materials are selected from the group consisting of a population of isolated naturally occurring cells, and cells in a tissue section.

* * * * *